United States Patent

Theodoropulos

Patent Number: 4,933,352
Date of Patent: Jun. 12, 1990

[54] BI-FUNCTIONAL CARBAMATES OF 2-UREADO-PYRIDINE COMPOUNDS

[76] Inventor: Spyros Theodoropulos, 2964 Hickory St., Yorktown Heights, N.Y. 10598

[21] Appl. No.: 33,593

[22] Filed: Mar. 31, 1987

[51] Int. Cl.$^5$ .......................................... C07D 213/53
[52] U.S. Cl. ................................. 514/336; 514/345; 514/349; 514/350; 514/352; 546/283; 546/284; 546/296; 546/297; 546/293; 546/305
[58] Field of Search ............... 546/283, 284, 296, 297, 546/293, 305; 514/336, 345, 349, 350, 352

[56] References Cited

U.S. PATENT DOCUMENTS 3,961,063  6/1976  Parish ................................. 546/283

FOREIGN PATENT DOCUMENTS 48667  3/1987  Japan ................................. 546/297

Primary Examiner—Mary C. Lee
Assistant Examiner—Zinna Northington-Davis
Attorney, Agent, or Firm—William R. Moran

[57] ABSTRACT

Novel carbamates of 2-ureado-6-hydroxy-pyridines have the structural formula

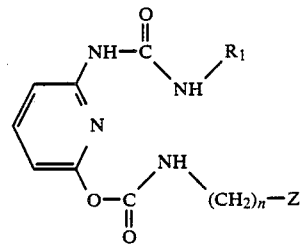

wherein n is 0 to 20; $R_1$ is hydrogen, alkyl which may be substituted, aryl which may be substituted; $R_2$ is hydrogen, halogen, carboxylic, $SO_3H$, $NO_2$, alkyl or aryl; $R_3$ and $R_4$ have the same meaning as $R_2$; Z is $N=C=O$, $N=C=S$, carboxylic, primary or secondary amine and when n=0, Z may be

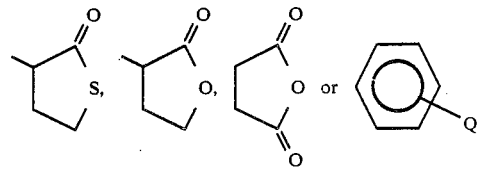

wherein Q is hydroxyl, amino, carboxylic, sulfhydryl, isocyanato or isothiocyanato. The carbamates of 2-ureado-6-hydroxypyridines react with compounds of interest to form derivatives which will chelate metal ions such as radionuclides or lanthanides, resulting in the radioisotopic or fluorescent labeling of the compounds.

7 Claims, No Drawings

BI-FUNCTIONAL CARBAMATES OF 2-UREADO-PYRIDINE COMPOUNDS

FIELD OF THE INVENTION

This invention relates to novel carbamates of 2-ureado-6-hydroxypyridine. The ureado-carbamates of the invention are strong chelating agents which form stable chelates with various metal ions such as rare earth and transition metals useful in inter alia industrial extraction and purification or in ore analysis by well-known techniques. Moreover, the 2-ureado-6-pyridine carbamates, according to this invention, are bi-functional making them useful inter alia in radioisotopic and fluorescent labeling of organic substrates. These bi-functional carbamates of 2-ureado-6-pyridinol have the ability to react with compounds of biological or clinical interest to form derivatives which will chelate with suitable metal ions such as radionuclides or lanthanides, resulting in the radioisotopic or fluorescent labeling of the compounds.

The bi-functionality of the novel carbamates according to the invention make them particularly useful in analytical techniques for the detection and measurement of biological and clinical compounds of interest. Typical examples of such compounds are bacteria, viruses, protozoa, rickettsia, amino acids, peptides, proteins, enzymes, hormones and blood groups. The novel carbamates are also intended, in view of their peculiar bi-functionality, for use as imaging agents for investigating the function of organs in animals, including man. Furthermore, these bi-functional chelating agents can be used for the radioisotopic labeling of biological molecules.

BACKGROUND OF THE INVENTION

It is known that chelating agents such as ethylenediaminetetraacetic acid (EDTA), when chelated with a radionuclide, can be used in organ imaging. However, the complex of EDTA and a radionuclide is of limited use in certain organs where lipo-solubility is necessary.

It is known that fluorescent groups such as fluorescein isothiocyanate can be introduced into biological or clinical compounds of interest. Analytical techniques employing fluorescein frequently lack the requisite sensitivity for the detection and measurement of nanomolar or picomolar levels of organic substrates. The lack in sensitivity of techniques which employ fluorescein is believed to be due to the high fluorescence background of biological fluids and to fluorescein's high degree of overlap in fluorescent excitation and emission spectra.

It is an object of the present invention to provide carbamate compounds of 2-ureado-6-hydroxypyridine which are strong chelating agents suitable for forming stable chelates, particularly with the rare earths, transition metals and radionuclides.

It is also an object of the present invention to provide novel bi-functional carbamates of 2-ureado-6-hydroxypyridine which may be readily coupled to compounds of clinical or biological interest to provide derivatives which form stable complexes with suitable metal ions and which exhibit radioactivity or fluorescence. An object of this invention is to provide radioisotopic labeled compounds which exhibit rapid preferential location in animals regardless of liposolubility. It is a further object of the invention to provide fluorescent labeled compounds which circumvent the overlap of the excitation and emission spectra of known compounds and which exhibit limited background fluorescence. A further object of this invention is to provide novel chelates which will exhibit distinct fluorescence excitation and emission spectra corresponding to that of the specific metal ion which is chelated, which chelates are stable and not deleterious to the biological compounds of interest. Yet another object of this invention lies in the coupling of the novel moieties to form adducts with a broad spectra of biological and clinical compounds by facile and gentle chemical reactions.

SUMMARY OF THE INVENTION

The 2-ureado-6-hydroxypyridine carbamates according to the invention have the structural formula

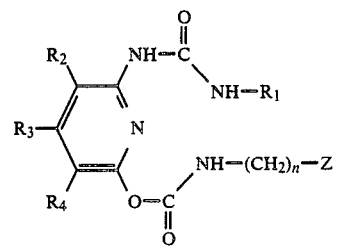

wherein n is 0 to 20; $R_1$ is hydrogen, alkyl which may be substituted, or aryl which may be substituted; $R_2$ is hydrogen, alkyl, aryl, halogen, carboxylic, $SO_3H$, or $NO_2$; $R_3$ and $R_4$ have the same meaning as $R_2$; Z is $N{=}C{=}O$, $N{=}C{=}S$, carboxylic, primary or secondary amine, and when n=0, Z may be

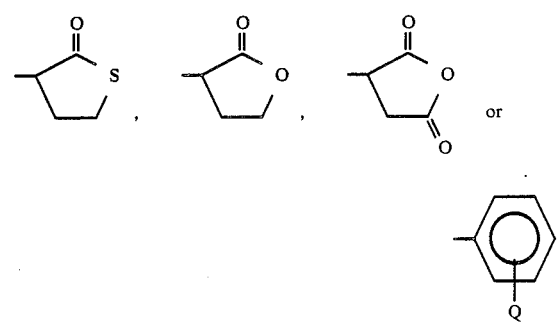

where Q is hydroxy, amino, carboxylic, sulfhydryl, isocyanato or isothiocyanato.

As previously set forth, the excellent chelating properties of the carbamates of 2-ureado-6-hydroxypyridine, according to the invention, make them suitable for any known use where the formation of a stable chelate is desirous. For example, in fluorescent labelling techniques, such as fluorescent immunoassays, the chelated derivatives of the invention in remarkable contrast to the prior art exhibit little decay or loss of fluorescence and exhibit distinct separation of excitation and emission spectra.

The novel carbamates of 2-ureado-6-hydroxypyridine of the present invention can be readily chelated with radioisotopic elements to provide radioisotopic probes which can be used as imaging agents for investigating the functioning of organs in animals including man. Furthermore, these radioactive probes can be used as therapeutic agents when short-lived radioactive nuclides can be localized in target areas.

DETAILED DESCRIPTION OF THE INVENTION

The carbamate compounds of 2-ureado-6-hydroxypyridine according to the invention are bi-functional. The 2-ureado-6-carbamato-pyridine moiety represented structurally as

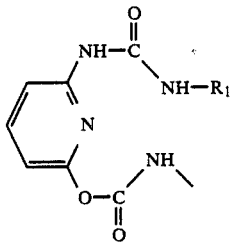

acts as an ideal chelating agent due to the stability of the resulting complex. The remaining moiety of the invention compounds represented by the radical —(CH$_2$)$_n$—Z where Z is an isothiocyanate, isocyanate, lactone or thiolactone moiety provides an active hydrogen bonding site and functions most suitably to promote coupling of the carbamate with other compounds of interest, including organic substrates. Depending upon the particular ureado-carbamate, the stable chelate formed may be either an ionic or coordinate bonded complex.

The 2-ureado-6-carbamato pyridines of the invention are synthesized from 2-amino-6-hydroxypyridine in three steps. For example, the reaction of 2-amino-6-hydroxypyridine with a silylating agent such as hexamethyldisilazane affords a hydroxy blocked compound. An example is illustrated in the following equation:

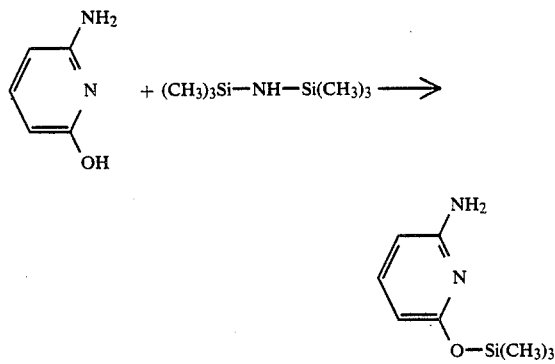

This reaction is optionally performed in the presence of a solvent which is inert to the reaction partners, such as benzene, toluene, xylene, pyridine, or aliphatic or aromatic chlorinated hydrocarbons as esters, ketones, amides or ethers with methylene chloride being the preferred solvent. The temperature employed in the reaction may range from 5° to 200° C., with ambient temperature being preferrable.

While the hexamethyldisilazane route has been employed, other silylating agents such as trimethylsilylacetamide, trimethylsilyltrifluoroacetamide or trimethylsilylchloride can be used. The use of trimethylsilylchloride for the silylation step may afford the ditrimethylsilylated compound in which both the hydroxy and the amine group at the 2-amino-6-hydroxypyridine have been silylated. The following reaction for the trimethylsilylchloride method is illustrated:

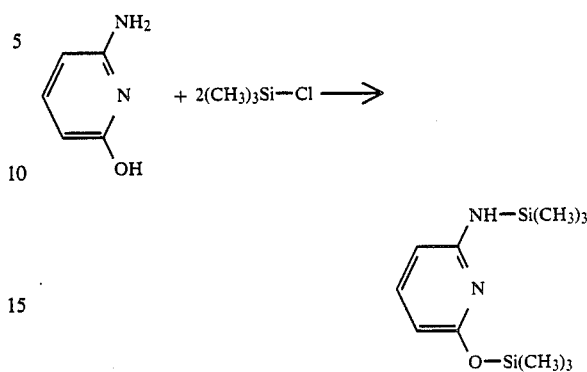

It has been found that trimethylsilylation of the hydroxy group blocks its nucleophylic reactivity while the resulting trimethylsilylamine enhance the nucleophylic reactivity of the amine group against electrophyles. It is therefore of no disadvantage to disilylate the 2-amino-6-hydroxypyridine in an effort to carry reactions of the amine group of the compound if one so wishes.

The resulting 2-amino-6-trimethylsilyloxypyridine obtained from the silylation reaction has been used to synthesize the 2-ureado-6-hydroxypyridine compounds of the invention. For example the reaction of 2-amino-6-trimethylsiloxy-pyridine with isocyanates of the general formula

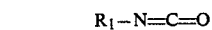

$$R_1-N=C=O$$

wherein R$_1$ is alkyl which may be substituted, or aryl which may be substituted. An example is illustrated in the following equation:

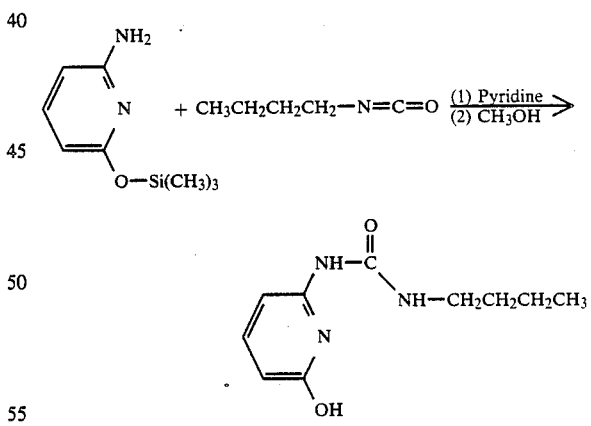

The reaction with isocyanates is preferably carried out in the presence of a solvent which is inert to the reaction partners such as aromatic hydrocarbons, aliphatic or aromatic chlorinated hydrocarbons such as methylene chloride or chlorobenzene, ethers, ketones, amides or pyridine. The temperature employed may range from 5° to 150° C. with ambient temperature being preferable. Deblocking of the 6-hydroxyl group can be easily achieved by the addition of alcohol or water, with known techniques such as crystallization or liquid or thin-layer chromatography can be employed for the purification.

While the isocyanate route of urea synthesis is preferred, the 6-hydroxy-2-pyridyl ureas can be synthesized by alternative methods utilizing either phosgene or chloroformic acid esters. In the phosgene method, an amine of the general formula

R$_1$—NH$_2$ wherein R$_1$ as defined above, is reacted with phosgene to form the carbamic acid chloride. The so formed carbamic acid chloride is then reacted in situ with 6-trimethylsilyloxy-2-aminopyridine to form the desired urea.

The chloroformic acid method involves the reaction of 6-trimethylsilyloxy-2-aminopyridine with chloroformic acid esters, such as ethylchloroformate, benzylchloroformate or isobutylchloroformate, and then reacting the product obtained with an amine of the general formula:

R$_1$—NH$_2$ wherein R$_1$ is as defined above.

The bifunctional carbamates of 2-ureado-6-hydroxypyridine of the invention are synthesized using known techniques. For example, by the reaction of 2-ureado-6-hydroxypyridine, whose synthesis is described above with a bi-functional isocyanate of the general formula:

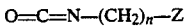

O=C=N—(CH$_2$)$_n$—Z wherein when n is O, Z is thiolactone, lactone or succinic anhydride, and when n is 1 to 20, Z is isocyanate, isothiocyanate, blocked carboxylic or benezene derivative such as

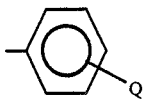

where Q is blocked primary or secondary amine, blocked carboxylic, isocyanate or isothiocyanate, is preferred.

An example is illustrated in the following equation:

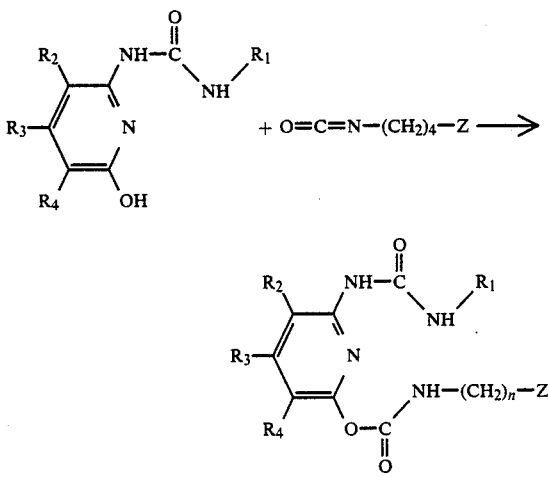

The synthesis is optionally performed in the presence of a solvent which is inert to the isocyanato radical such as chlorinated aromatic or aliphatic hydrocarbons, aromatic hydrocarbon, e.g., benzene, toluene, xylene or esters, ketones and amides. The preferred solvent is pyridine. The temperature employed in the synthesis may range from 5° to 150° C. with ambient temperature being preferred. Also, if desired, any of the several types of catalysts known to be useful in forming urethanes can be employed. Useful catalysts include tertiary amines, salts or organic acids with a variety of metals such as alkali metals and the like.

While the isocyanate route of carbamate synthesis is preferred, the bi-functional carbamate of 2-ureado-6-hydroxypyridine can be synthesized by alternate methods, utilizing either phosgene or chloroformic acid esters which are described in the 6-hydroxy-2-pyridyl urea synthesis. In the phosgene method, an amine of the general formula

H$_2$N—(CH$_2$)$_n$—Z wherein n is 0 to 20 and Z is as defined above, is reacted with phosgene to form carbamic acid chloride. The so-formed carbamic acid chloride is then reacted in situ with 2-ureado-6-hydroxypyridine to form the desired carbamate.

The method utilizing chloroformic acid esters involves the reaction of 2-ureado-6-hydroxypyridine with isobutylchloroformate and then reacting the resulting product with an amine of the general formula

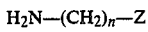

H$_2$N—(CH$_2$)$_n$—Z wherein n is 0 to 20 and Z is as defined above. Other chloroformic acid esters such as benzylchloroformate, etherchloroformate and the like can be utilized in this method of carbamate synthesis.

The 2-ureado-6-hydroxypyridine carbamates of the invention may be reacted with any compound of interest capable of reacting with the Z radical. For example, any compound containing (in the clinical sense) an active hydrogen group may be coupled to the carbamates, e.g., any compound containing a hydroxyl, amino, sulfhydryl or carboxylic group can be utilized. Accordingly, with regard to organic or biological compound of interest, a wide number of amino acids, peptides, proteins, enzymes, steroids, drugs, pesticides, various natural products, plant and animal hormones, polyamines, viruses, bacterial cells and other matabolites contain groups reactive with the Z radicals.

The carbamates of 2-ureado-6-hydroxypyridine can be bound to organic substrates by utilizing known process conditions. It is suitable, for example, to prepare the adduct by reaction in a solvent, if desired, at a temperature ranging from 0° to about 150° C. Representative examples of useful solvents include pyridine, formamide, tetrahydrofuran, triethylamine, dimethylformamide, ethers, methylene chloride, water and aqueous media.

The conditions selected should be such as to insure that the structure of the compound of interest will not be degraded or otherwise adversely effected. For this reason, it is preferable to utilize as mild conditions as possible.

The 2-ureado-6-hydroxypyridine carbamates of the invention may be coupled to biological molecules or clinical compounds of interest through the Z moiety in various ways to form adducts. For example, when the Z moiety is isothiocyanate, coupling occurs readily with proteins, such as antibodies, enzymes and amino acids and other biological molecules having an amine group which are receptive to an amide linkage. The following reaction for the isothiocyanato carbamate is illustrated:

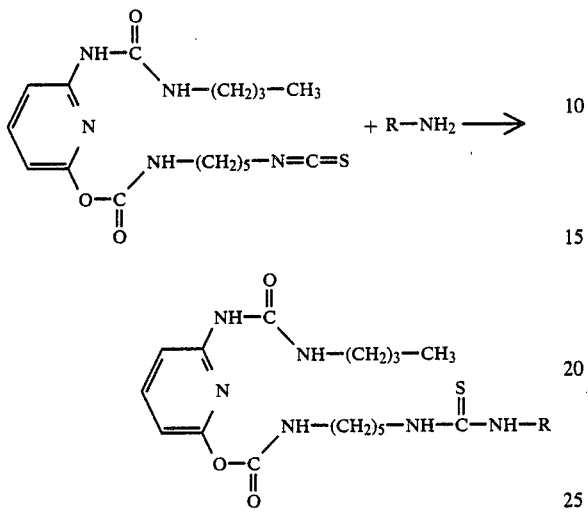

where R is an organic substrate containing a functional amine group having an active hydrogen. The coupling is carried out in a variety of solvents depending on the nature of the organic substrate. Coupling with proteins, for example, is carried out in buffers such as carbamates, phosphates or citrates. The pH of the reaction may range from 1 to 12, but a pH of 8 to 10 is preferred. The reaction time and temperature are approximately selected depending on the stability and nature of the protein. The preferred reaction time is 1 to 24 hours and the preferred temperature is about 4° C. to ambient.

Since proteins may have more than one amino group, it is possible that more than one 2-ureado-6-carbamatopyridines can be coupled. The coupling of one to five 2-ureado-pyridine carbamates is preferred. The ratio of 2-ureado-6-hydroxypyridine carbamates to the number of proteins coupled can be controlled by the amount of the pyridyl carbamate used.

Coupling with organic substrates bearing functional amino groups and which are not susceptible to organic solvents is carried out in pyridine, dimethylformamide, chlorinated hydrocarbons, ethers, ureas, amides and a variety of solvents which are inert to the reaction partners.

When the Z moiety is thiolactone, coupling occurs readily with proteins and other biological molecules having an amine group with an active hydrogen, which are receptive to an amide linkage. The following equation illustrates this type of reaction:

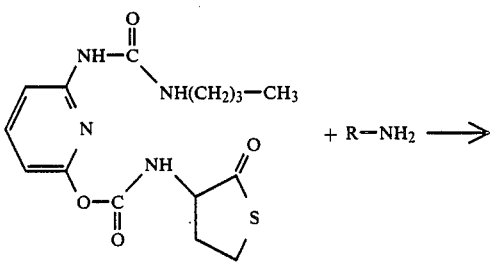

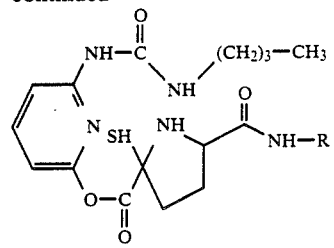

where R is an organic substrate containing a functional amine group having an active hydrogen. The conditions for the thiolactone coupling are similar to the conditions used for the coupling of isothiocyanato-2-ureado-pyridyl carbamate.

When the Z moiety is isocyanate, as in 2-ureado-6-isocyanatohexyl-pyridyl-carbamate, the resulting carbamate is wellsuited to coupling with biological molecules which have hydroxyl reactive groups such as digoxin, cortisol, estradiol and, in general, drugs or hormones having reactive hydroxyl groups. This, however, does not exclude coupling to compounds with other reactive groups. Typically, for example, any compound containing an hydroxyl, amino, sulfhydryl or carboxylic group can be utilized. For example, ethanol can be coupled to 2-ureado-6-isocyanatohexyl-pyridyl-carbamate in accordance with the invention by a carbamate bond as shown in the following equation:

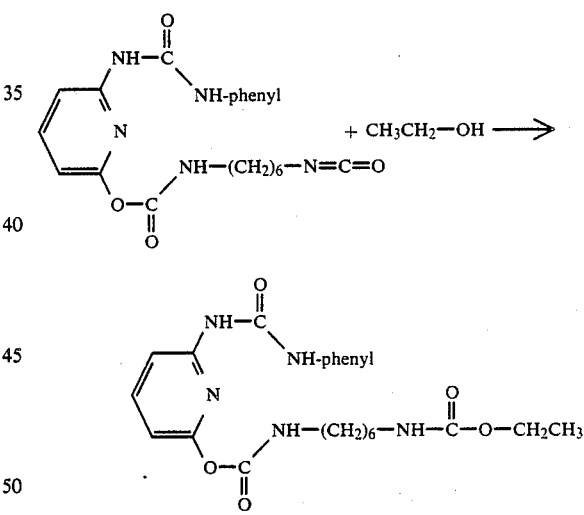

Many compounds of interest contain more than one radical reactive with the isocyanate moiety, resulting in the formation of more than one species. This can be minimized and even avoided by utilizing particular blocking and deblocking techniques. For example, 11-amino-undecanoic acid possesses one amino and one carboxylic group, both of which can react with isocyanate radicals. In order to minimize the reactive sites, it is necessary to block the carboxylic group with trimethylsilyl radicals. It has been discovered that the employment of this procedure results only in the production of a single species consistent with a structure having a 2-ureado-6-carbamatopyridine linked to the 11-amino group of the 11-amino-undecanoic acid. Deblocking of the carboxylic group is accomplished by using water or methanol. Where the reaction provides more than one species, conventional separation techniques (e.g., thin layer chromatography or crystallization) can be employed.

The 2-ureado-6-carbamatopyridine moiety of this invention is receptive to chelation and may be advantageously utilized in any of the several known techniques involving radioisotopic or fluorescent competitive binding to detect and measure the compound of interest. Adducts of 2-ureado-6-carbamatopyridine and biological molecules complexed with radionuclides such as technetium 99 can be used in vivo for diagnostic or therapeutic purposes. The particular 2-ureado-6-carbamatopyridine adducts used will be dependent upon the type of tagging required by the technique of choice and the technique selected will be determined by the results required. Suitable ions, including radioisotopic ions, for chelating the compounds of the invention are ions of the lanthanide series of elements, e.g., the rare earths and ions of the transition metals. Illustrative examples are lanthanum, indium, europium, scandium, terbium, beryllium, technisium, cobalt and gallium ions. It is preferred to use a lanthanide ion for fluorescent labeling of organic substrates. It is preferred to use technisium-99 or indium-111 ions for radioisotopic labeling of organic substrates. The following examples are illustrative, but not in limitation, of the present invention:

EXAMPLE 1

2-(N-butylureado)-6-hydroxypyridine

The chemical formula of 2-(N-butylureado)-6-hydroxypyridine is shown below.

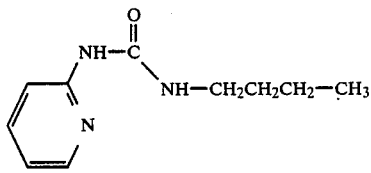

A mixture of 2.2 grams (0.02 mols) of 2-amino-6-hydroxypyridine suspended in 20 milliliters of dry methylene chloride and 9.0 milliliters of hexamethyldisilazane was stirred at ambient temperature for about 24 hours. The homogeneous reaction mixture formed was evaporated to dryness using trap to trap distillation and the resulting residue was dissolved in 10 milliliter of dry pyridine. To this was added 2.5 milliliter (0.022 mols) of n-butylisocyanate and the mixture stirred at ambient temperature for about 24 hours. The pyridine and excess n-butylisocyanate was then removed in vacuo at ambient temperature and the crude reaction mixture was washed with water. 3.1 grams of product dried in a stream of air was obtained. The product analyzed by infrared spectroscopy showed bands at (nujol) 3.0 (NH), 3.10-3.15 (OH), 5.88 and 6.03 (urea carbonyl), 6.3μ (aromatic).

EXAMPLE 2

2-(N-phenylureado)-6-hydroxypyridine

The chemical formula of 2-(N-phenylureado)-6-hydroxypyridine is shown below.

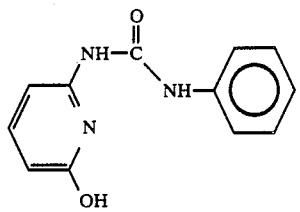

A mixture of 1.1 grams (0.01 mols) of 2-amino-6-hydroxypyridine suspended in 10 milliliter of dry pyridine and 5.0 milliliter of hexamethyldisilazane was stirred at ambient temperature for about 24 hours. The solvent and excess of hexamethyldisilazane was then removed using trap to trap distillation and the resulting residue was dissolved in 10 milliliters of dry Pyridine. To this was added 1.5 milliliters (0.013 mols) of phenylisocyanate and the mixture stirred at ambient temperature for about 24 hours. The pyridine was then removed in vacuo and the crude reaction product crystallized from methanol gave 2.1 grams of product. The product analyzed by infrared spectroscopy showed bands at (nujol) 3.03 (NH), 6.0 (urea carbonyl), 6.25, 6.40, 6.53, 7.58, 7.9, 8.13, 8.30, 8.70 μ.

EXAMPLE 3

2-(N-butylureado)-6-(N-5-isothiocyanatopentylcarbamato)-pyridine

The chemical formual of 2-ureado-6-isothiocyanatopentylcarbamato pyridine is shown below.

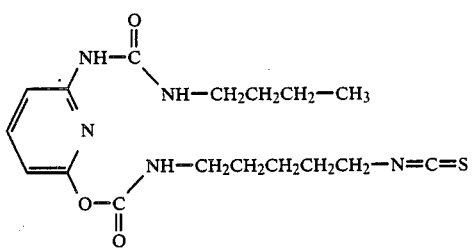

A mixture of 210 milligrams (0.001 mols) of 2-(N-butylureado)-6-hydroxypyridine and 0.3 milliliter of 1-isocyanato-5-isothiocyanato-pentane were mixed in 3.0 milliliter of dry pyridine and stirred at ambient temperature for five days. The pyridine was then removed in vacuo and the crude reaction mixture was washed with 50% ether-hexane to remove excess of 1-isocyanato-5-isothiocyanatopentane. 350 milligrams of solid product was obtained. The product characterized by infrared spectroscopy showed bands at (nujol) 3.0 (NH), 4.75 (N═C═S), 5.80 (carbamate carbonyl), 5.90μ (urea carbonyl).

EXAMPLE 4

2-(N-phenylureado)-6-(N'-isocyanatohexylcarbamato)-pyridine

The chemical formula of 2-(N-phenylureado)-6-(N'-isocyanatohexylcarbamato)-pyridine is shown below.

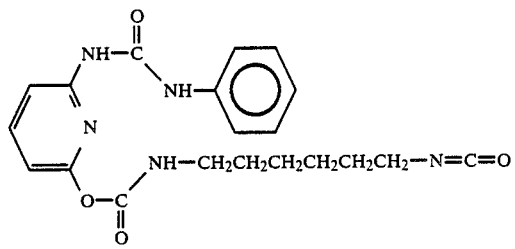

A mixture of 100 milligrams of 2-(N-phenylureado)-6-hydroxypyridine and 1.0 milliliter of 1,6-diisocyanatohexane (excess) were mixed in 10 milliliters of dry pyridine and the mixture was allowed to stir at ambient temperature for three days. The pyridine was then removed in vacuo at ambient temperature and the crude reaction mixture was washed with dry ether to remove unreacted diisocyanato hexane.

Since the isocyanato moiety was susceptible to hydrolysis, the product was used in its crude form. 160 Milligrams of 2-(N-phenylureado)-6-(N'-isocyanatohexylcarbamato)-pyridine was obtained. IR (pyridine) analysis showed bands at 4.45 (N=C=O), 5.7 and 5.8μ (carbamate and urea carbonyls).

EXAMPLE 5

Coupling of 2-(N-phenylureado)6-(N'-isocyanatohexylcarbamato)-pyridine to ethanol The chemical formula of the adduct formed by coupling 2-(N-phenylureado)6-(isocyanatohexylcarbamato)-pyridine to ethanol is shown below.

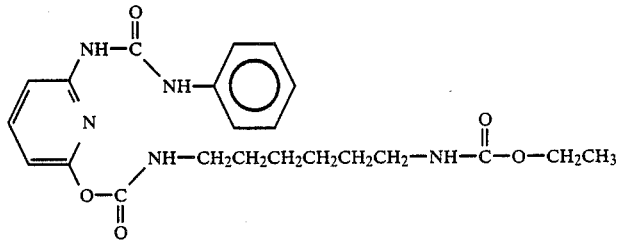

A mixture of 160 milligrams of 2-(N-phenylureado)-6-(N'-isocyanatohexylcarbamato)-pyridine, prepared in accordance with Example 4, was mixed with 5.0 milliliters of absolute ethanol in 3.0 milliliters of dry pyridine and the mixture stirred at ambient temperature for about 24 hours. The pyridine and other volatiles were removed in vacuo and gave 185 milligrams of the product. The product characterized by infrared spectroscopy (neat smear) gave bands at 3.0 (NH), 5.9 broad (carbonyls), 6.45, 7.9, 8.75, and 9.7μ.

EXAMPLE 6

2-(N-n-butylureado)-6-(N'-isocyanatohexylcarbamato)-pyridine

The chemical formula of 2-(N-n-butylureado)-6-(N'-isocyanatohexylcarbamato)-pyridine is shown below.

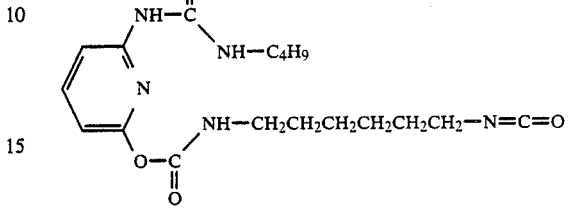

A mixture of 210 milligrams of 2-(N-n-butylureado)-6-hydroxypyridine prepared in accordance with Example 1 and 0.5 milliliters of 1,6-diisocyanatohexane dissolved in 5.0 milliliters of dry pyridine was allowed to stir at ambient temperature for 3 days. The pyridine was then removed in vacuo and the crude reaction mixture was washed with hexane two times and with 50% hexane-ether to remove unreacted diisocyanatohexane.

Since the isocyanato moiety was susceptible to hydrolysis, the product was used in its crude form. 350 Milligrams of 2-(N-n-butylureado)-6-(N'-isocyanatohexylcarbamato)-pyridine was obtained. IR (pyridine) analysis showed bands at 4.45μ (—N=C=O), 5.7μ (carbamate carbonyl), 5.9μ (urea carbonyl).

EXAMPLE 7

Coupling of 2-(N-n-butylureado)6-(N'-isocyanatohexylcarbamato)-pyridine to 11-aminoundecanoic acid The chemical formula of the adduct formed by coupling 2-(N-n-butylureado)-6-(N'-isocyanatohexylcarbamato)-pyridine to 11-aminoundecanoic acid is shown below.

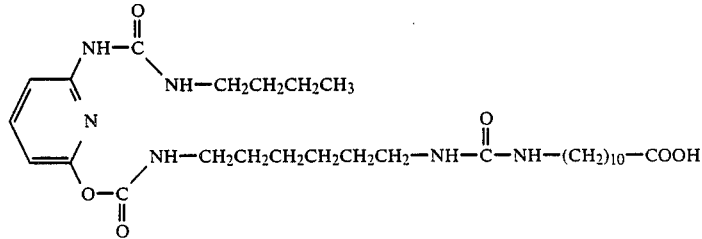

A mixture of 300 milligrams (0.0015 mols) of 11-aminoundecanoic acid suspended in 5 ml of dry pyridine and 1.0 milliliter of hexamethyldisilazane was allowed to stir at about 100° C. for one hour. The solvent and excess of hexamethyldisilazane were then removed using trap to trap distillation and the resulting residue was dissolved in 3.0 milliliter of dry pyridine. Using a syringe, the pyridine solution was transferred to a flask containing 350 milligrams of 2-(N-n-butylureado)-6-(N'-isocyanatohexylcarbamato)-pyridine prepared in accordance with Example 6. The mixture was stirred at ambient temperature for 48 days. The solvent was then removed in vacuo and the flask content was dissolved in methanol and filtered. The filtrate, evaporated to dryness, gave 470 mg of the adduct.

I claim:

1. 2-ureado-6-hydroxypyridines having the formula:

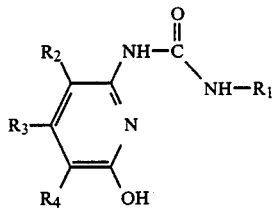

wherein $R_1$ is hydrogen, lower alkyl or phenyl; and $R_2$-$R_4$ represent hydrogen, lower alkyl, aryl, halogen, carboxyl, $SO_3H$ or $NO_2$.

2. Carbamates of 2-ureado-6-hydroxypyridine having the formula:

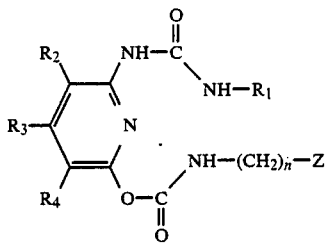

wherein $R_1$-$R_4$ are the same as defined in claim 1; n is 0 to 20 and Z is —N=C=O, —N=C=S, carboxyl, primary or secondary amine; and n is 0, Z may be

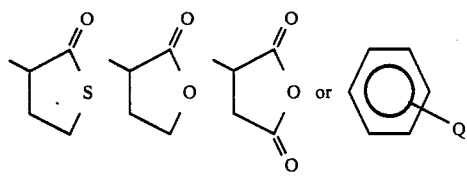

wherein Q is hydroxyl, amino, carboxylic, sulfhydryl, isocyanato or isothiocyanato.

3. 2-Ureado-6-hydropyridine carbamates bound to an organic substrate forming adducts having the formula:

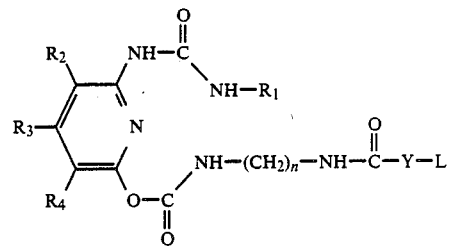

wherein n, $R_1$, $R_2$, $R_3$, and $R_4$ are the same as defined in claim 1; Y is a secondary amino or sulfur; and L is an biological organic substrate linked to said carbamate by reaction of said carbamate with a substrate containing a functional group having an active hydrogen selected from the group consisting of hydroxyl, amino, sulfhydryl and carboxyl.

4. 2-Ureado-6-hydropyridine carbamates bound to an organic substrate forming adducts having the formula:

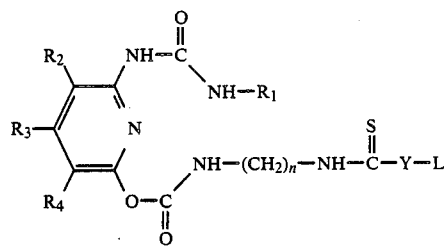

wherein n, $R_1$, $R_2$, $R_3$, and $R_4$ are the same as defined in claim 1; Y is a secondary amino or sulfur; and L is an biological organic substrate linked to said carbamate by reaction of said carbamate with a substrate containing a functional group having an active hydrogen selected from the group consisting of hydroxyl, amino, sulfhydryl and carboxyl.

5. 2-Ureado-6-hydropyridine carbamates bound to an organic substrate forming adducts having the formula:

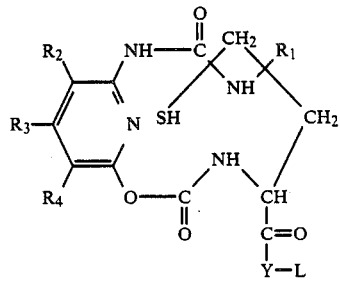

wherein n, $R_1$, $R_2$, $R_3$, and $R_4$ are the same as defined in claim 1, Y is a secondary amino or sulfur; and L is an biological organic substrate linked to said carbamate by reaction of said carbamate with a substrate containing a functional group having an active hydrogen selected from the group consisting of hydroxyl, amino, sulfhydryl and carboxyl.

6. An adduct of 2-ureado-6-hydroxypyridine carbamate having the formula:

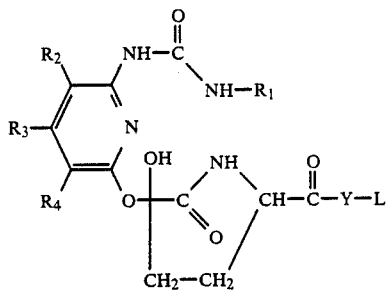

wherein $R_1$, $R_2$, $R_3$, and $R_4$ are the same as defined in claim 1; Y is a secondary amino or sulfur; and L is an biological organic substrate linked to said carbamate by reaction of said carbamate with a substrate containing a functional group having an active hydrogen selected from the group consisting of hydroxyl, amino, sulfhydryl and carboxyl.

7. An adduct of 2-ureado-6-hydroxypyridine carbamate having the formula:

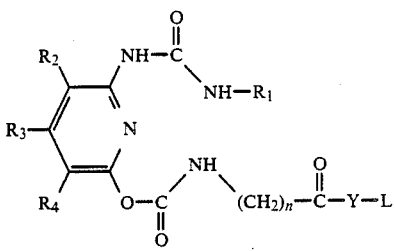

wherein n, $R_1$, $R_2$, $R_3$, and $R_4$ are the same as defined in claim 1; Y is a secondary amino or sulfur; and L is an biological organic substrate linked to said carbamate by reaction of said carbamate with a substrate containing a functional group having an active hydrogen selected from the group consisting of hydroxyl, amino, sulfhydryl and carboxyl.

* * * * *